(12) United States Patent
Petisce

(10) Patent No.: US 8,895,252 B2
(45) Date of Patent: Nov. 25, 2014

(54) HIGH ENERGY RADIATION INSENSITIVE ANALYTE SENSORS

(75) Inventor: James R. Petisce, Westford, MA (US)

(73) Assignee: Edwards Lifesciences Corporation, Irvine, CA (US)

(*) Notice: Subject to any disclaimer, the term of this patent is extended or adjusted under 35 U.S.C. 154(b) by 0 days.

(21) Appl. No.: 13/580,628

(22) PCT Filed: Mar. 10, 2011

(86) PCT No.: PCT/US2011/027882
§ 371 (c)(1),
(2), (4) Date: Nov. 19, 2012

(87) PCT Pub. No.: WO2011/115809
PCT Pub. Date: Sep. 22, 2011

(65) Prior Publication Data
US 2013/0189720 A1   Jul. 25, 2013

Related U.S. Application Data

(60) Provisional application No. 61/314,538, filed on Mar. 16, 2010.

(51) Int. Cl.
*G01N 33/53* (2006.01)
*G01N 33/567* (2006.01)
*C12M 1/34* (2006.01)
*C12M 3/00* (2006.01)
*G01N 27/327* (2006.01)
*A61B 5/1486* (2006.01)
*C12Q 1/26* (2006.01)

(52) U.S. Cl.
CPC ............. *C12Q 1/26* (2013.01); *A61B 2562/18* (2013.01); *G01N 27/327* (2013.01); *A61B 5/14865* (2013.01)
USPC .................... 435/7.1; 435/287.1; 435/287.4

(58) Field of Classification Search
None
See application file for complete search history.

(56) References Cited

U.S. PATENT DOCUMENTS

| 5,804,048 A | 9/1998 | Wong et al. | |
|---|---|---|---|
| 2007/0111196 A1* | 5/2007 | Alarcon et al. | 435/4 |
| 2007/0128681 A1* | 6/2007 | Barman et al. | 435/14 |
| 2008/0197024 A1* | 8/2008 | Simpson et al. | 205/778 |

OTHER PUBLICATIONS

Ciba Specialty Chemicals "CIBA CHIMASSORB 944" Pringed May 2002, 3 pgs.*
Supplemental European Search Report, Feb. 7, 2014, 5 pages.
Chinese Office Action, Aug. 5, 2013, 9pgs, English translation provided.

* cited by examiner

*Primary Examiner* — Thane Underdahl
(74) *Attorney, Agent, or Firm* — Michael Crapenhoft

(57) ABSTRACT

Enzyme based analyte sensors having radiation stabilizing agents are disclosed and described. More particularly, devices comprising a radiation stabilizing agent and methods for stabilizing sensors to high energy radiation sterilization are disclosed and described.

13 Claims, 3 Drawing Sheets

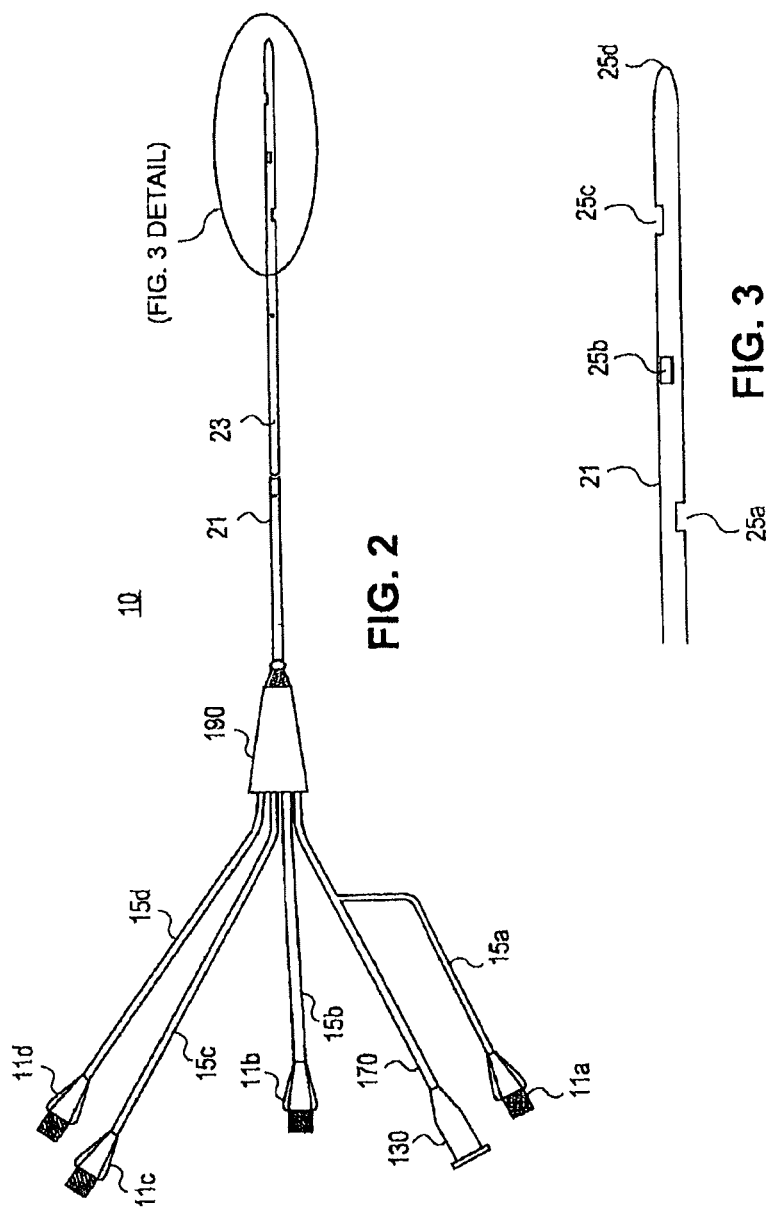

HIGH ENERGY RADIATION INSENSITIVE ANALYTE SENSORS

TECHNICAL FIELD

The present disclosure relates generally to analyte sensors comprising radiation stabilizing agents for stabilizing analyte sensors exposed to radiation. More particularly, the present disclosure relates to analyte sensors comprising radiation stabilizing agents for stabilizing analyte responsive enzymes exposed to sterilizing radiation.

BACKGROUND

Some analyte sensors utilize analyte responsive enzymes to directly or indirectly detect analytes. These enzymes are typically immobilized or encapsulated in or between one or more membranes or layers of the analyte sensor. In vivo sensors, which are in contact with blood and tissue, the sensor and its analyte responsive enzyme preferably is provided sterilized. Commonly used methods of sterilization such as exposing the device to ethylene oxide, or high energy radiation, for example gamma rays, electron beams, ultraviolet light, or x-rays is undesirable for analyte responsive enzymes. The high-energy radiation can affect all of the sensor's components by creating free radicals, which can chemically change one or more of the sensor's components, including the enzyme.

SUMMARY

Disclosed and described herein are enzyme-based analyte sensors and sensor assemblies comprising radiation stabilizing agents and methods of providing stabilization of the enzyme and/or the one or more membrane layers subjected to radiation sterilization.

In a first embodiment, an electrochemical analyte sensor is provided. The enzyme-based analyte sensor comprises at least one electrode and at least one enzyme and at least one radiation stabilizing agent.

In one aspect of the first embodiment, the radiation stabilizing agents include hindered light amine stabilizers, antioxidants, vitamins, and combinations thereof.

In a second aspect alone or in combination with any one of the previous aspects of the first embodiment, the hindered amine light stabilizer comprises one or more of polymethylpropyl 3-oxy-[4(2,2,6,6 tetramethyl) piperidinyl]siloxane (Uvasil 299); poly[[.beta.-[1,1,3,3-tetramethyl butyl)amino]-s-triazine-2,4-diyl][[2,2,6,6-tetramethyl-4-piperidyl)imino] hexamethylene[(2,2,6,6,-tetramethyl-4-piperidyl)imino]] (Chimassorb 944); 1,3,5-triazine-2,4,6-triamine, N,N'''-[1,2-ethanediylbis[[[4.6-bis[butyl(1,2,2,6,6-pentamethyl-4-piperidinyl)amino]-1,3,5-triazine-2-yl]imino]-3,1 propanedyl]]-bis[N',N''-dibutyl-N',N''-bis(1,2,2,6,6-pentamethyl-4-piperidinyl)- (Chimassorb 119); alkyl substituted piperidinyl alkandioic acid esters; bis(1,2,2,6,6-pentamethyl-4-piperidinyl)sebacate; bis-(1-octyloxy-2,2,6,6,tetramethyl-4-piperidinyl)sebacate (Tinuvin 123); bis(1,2,2,6,6-pentamethyl-4-piperidinyl)-[[3,5-bis(1,1-dimethylethyl)-4-hydroxyphenyl]methyl]butylmalonate (Tinuvin 144); 1,1'-(1,2-ethanediyl)bis(3,3,5,5-tetramethylpiperazinone); dimethyl succinate polymer with 4-hydroxy-2,2,6,6-tetramethyl-1-piperidineethanol (Tinuvin 622); poly((6-((1,1,3,3-tetramethylbutyl)amino)-s-triazine-2,4-diyl)(t-(2,2,6,6-tetramethyl-4-piperidyl)iminohexa-methylene((2,2,6,6-tetramethyl-4-piperidyl)imino)) and dimethyl succinate polymer with 4-hydroxy 2,2,6,6-tetramethyl-1-piperidineethanol (Tinuvin 783); 1,3,5-triazine-2,4,6-triamine, N2,N2'-1,2-ethanediylbis[N2-[3-[[4,6-bis[butyl(1,2,2,6,6-pentamethyl-4-piperidinyl)amino]-1,3,5-triazin-2-yl]amino] propyl]-N4,N6-dibutyl-N4,N6-bis(1,2,2,6,6-pentamethyl-4-piperidinyl)- (Lowilite 19); polymer of dimethyl succinate and 4-hydroxy-2,2,6,6-tetramethyl-1-piperidine ethanol (Lowilite 62); Bis(2,2,6,6-tetramethyl-4-piperidyl)sebacate (Lowilite 77); mixture of bis(1,2,2,6,6-pentamethyl-4-piperidinyl)sebacate and methyl(1,2,2,6,6-pentamethyl-4-piperidinyl)sebacate (Lowilite 92); or poly[[6-[(1,1,3,3-tetramethylbutyl)amino]-1,3,5-triazine-2,4-diyl]-[(2,2,6,6 tetramethyl-4-piperidyl)imino]hexamethylene[(2,2,6,6-tetramethyl-4-piperidyl)imino]] (Lowilite 94).

In a third aspect alone or in combination with any one of the previous aspects of the first embodiment, the radiation stabilizer comprises at least one of a polymeric hindered phenol, a polymeric aromatic amine, a polymer with thioester or phosphorous containing appendages, a polymeric hydroxylamine, a polymeric benzofuranone derivative, and polymeric acrylated bis-phenol.

In a fourth aspect alone or in combination with any one of the previous aspects of the first embodiment, the sensor further comprises an interference layer. The interference layer can comprise the radiation stabilizing agent.

In a fifth aspect alone or in combination with any one of the previous aspects of the first embodiment, the enzyme based analyte sensor further comprises a flux limiting membrane. The flux limiting membrane can comprise the radiation stabilizing agent.

In a sixth aspect alone or in combination with any one of the previous aspects of the first embodiment, the enzyme based analyte sensor is configured for a catheter.

In a seventh aspect alone or in combination with any one of the previous aspects of the first embodiment, the enzyme is presented in an enzyme layer, the enzyme layer comprising a hydrophilic polymer. The enzyme layer can comprise the radiation stabilizing agent.

In a second embodiment, an electrochemical enzyme-based analyte sensor is provided. The sensor comprises at least one electrode having an electroactive surface, an enzyme layer comprising at least one enzyme, at least one radiation stabilizer, at least one membrane layer, the membrane covering at least a portion of the electroactive surface.

In a third embodiment, a method of stabilizing enzymes subjected to radiation is provided. The method includes providing a sensor comprising a membrane applied to at least one electrode, the membrane comprising at least one enzyme and at least one radiation stabilizing agent, and subjecting the enzyme-based analyte sensor to high energy radiation. The enzyme-based sensor can be an intravenous blood glucose sensor (IVBG).

BRIEF DESCRIPTION OF THE DRAWINGS

FIG. 2 is a side view of a multi-lumen catheter with a sensor assembly according to an aspect disclosed and described.

FIG. 3 is a detail of the distal end of the multi-lumen catheter of FIG. 3 according to an aspect disclosed and described.

DETAILED DESCRIPTION

Figure 1A:
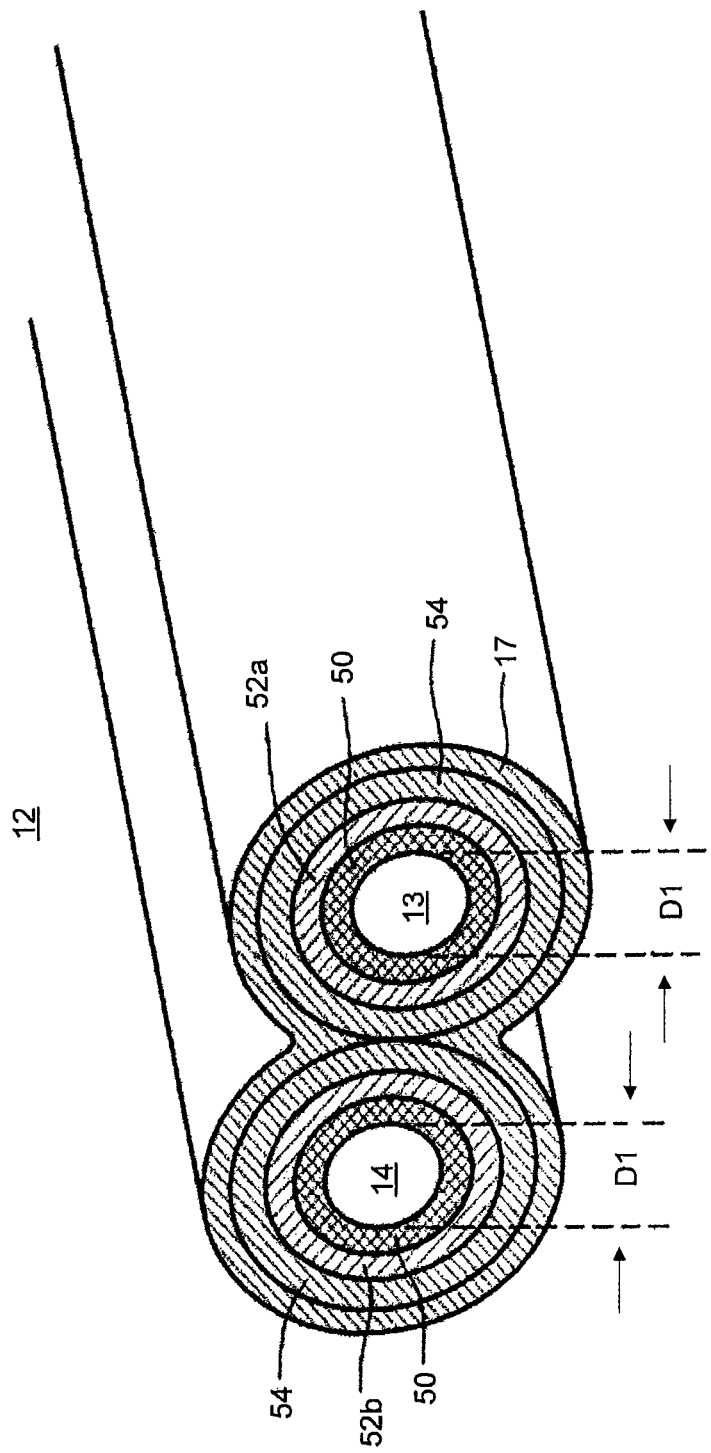
FIG. 1A shows an amperometric sensor having a working electrode and a reference electrode according to an aspect disclosed and described.

In enzyme based analyte sensors constructed for in vivo use, high energy radiation sterilization is employed to sterilize sensor prior to use. During sterilization by high energy radiation the enzyme can degrade resulting in, among other things, a loss in sensitivity and/or selectivity. Moreover, one or more of the membrane layers of the sensor can be affected by the high energy radiation, for example, the membrane layer can depolymerize or crosslink, resulting in a change in the diffusional properties of the one or more membrane layers. One or more of these events can occur during high energy radiation sterilization of the sensor, causing the enzyme to destabilize or diffusional properties to change, resulting in decreased analyte detection accuracy. The effects of radiation exposure can continue long after the sensor has been sterilized, which can further affect the quality of the sensors. Furthermore, other steps taken to prepare the sensor for use may also affect the stability of enzyme based sensors. Thus, disclosed herein are enzyme-based analyte sensors and sensor assemblies comprising radiation stabilizing agents and methods of providing stabilization of the enzyme and/or the one or more membrane layers subjected to radiation sterilization. More particularly, devices and methods for stabilizing enzymes exposed to radiation sterilization in a sensor comprising at least one enzyme and at least one radiation stabilizing agent are disclosed. The various embodiments disclosed herein describe analyte sensors that substantially prevent or reduce degradation of the enzyme and optionally, one or more of the membrane layers, upon exposure to high energy radiation. Moreover, enzyme based analyte sensors are pre-calibrated prior to sterilization by placing the sensor in a calibration solution. Any compounds in the sensor assembly that are not of a particular molecular weight or of a particular solubility may be washed away during pre-calibration. Thus, further disclosed and described herein is an enzyme based sensor comprising radiation stabilizing agents having sufficient molecular weight and solubility parameters to prevent the agents from being washed away (e.g., "non-fugitive radiation stabilizing agents") when subjected to a calibration solution or pre-calibration procedure.

The following description and examples illustrate some exemplary embodiments of the disclosed invention in detail. Those of skill in the art will recognize that there may be numerous variations and modifications of this invention that may be encompassed by its scope. Accordingly, the description of a certain exemplary embodiment is not intended to limit the scope of the present invention.

DEFINITIONS

In order to facilitate an understanding of the various aspects of the invention, the following are defined below.

The term "analyte" as used herein refers without limitation to a substance or chemical constituent of interest in a biological fluid (for example, blood) that may be analyzed. The analyte may be naturally present in the biological fluid, the analyte may be introduced into the body, or the analyte may be a metabolic product of a substance of interest or an enzymatically produced chemical reactant or chemical product of a substance of interest. Preferably, analytes include chemical entities capable of reacting with at least one enzyme and quantitatively yielding an electrochemically reactive product that is either amperometrically or voltammetrically detectable.

The phrases and terms "analyte measuring device," "sensor," and "sensor assembly" as used herein refer without limitation to an area of an analyte-monitoring device that enables the detection of at least one analyte. For example, the sensor may comprise a non-conductive portion, at least one working electrode, a reference electrode, and a counter electrode (optional), forming an electrochemically reactive surface at one location on the non-conductive portion and an electronic connection at another location on the non-conductive portion, and one or more layers over the electrochemically reactive surface.

The phrase "capable of" as used herein, when referring to recitation of function associated with a recited structure, is inclusive of all conditions where the recited structure can actually perform the recited function. For example, the phrase "capable of" includes performance of the function under normal operating conditions, experimental conditions or laboratory conditions, as well as conditions that may not or cannot occur during normal operation.

The term "cellulose acetate butyrate" as used herein refer without limitation to compounds obtained by contacting cellulose with acetic anhydride and butyric anhydride.

The term "comprising" and its grammatical equivalents, as used herein is synonymous with "including," "containing," or "characterized by," and is inclusive or open-ended and does not exclude additional, unrecited elements or method steps.

The phrases "continuous analyte sensing" and "continual analyte sensing" (and the grammatical equivalents "continuously" and continually") as used herein refer without limitation to a period of analyte concentration monitoring that is continuously, continually, and/or intermittently (but regularly) performed.

The phrase "continuous glucose sensing" as used herein refers without limitation to a period of glucose concentration monitoring that is continuously, continually, and/or intermittently (but regularly) performed. The period may, for example, at time intervals ranging from fractions of a second up to, for example, 1, 2, or 5 minutes, or longer.

The terms "crosslink" and "crosslinking" as used herein refer without limitation to joining (e.g., adjacent chains of a polymer and/or protein) by creating covalent or ionic bonds. Crosslinking may be accomplished by known techniques, for example, thermal reaction, chemical reaction or ionizing radiation (for example, electron beam radiation, UV radiation, X-ray, or gamma radiation). For example, reaction of a dialdehyde such as glutaraldehyde with a hydrophilic polymer-enzyme composition would result in chemical crosslinking of the enzyme and/or hydrophilic polymer (e.g., the formation of reaction products of the cross-linking agent and the enzyme and/or hydrophilic polymer).

The phrase "hydrophilic polymer-enzyme composition" refers without limitation to a physical or chemical mixture, a physical blend, a continuous or discontinuous phase, a micelle or a dispersion of at least one enzyme and at least one hydrophilic polymer. The hydrophilic polymer-enzyme composition may further include at least one protein, or a natural or synthetic material.

The phrase "electroactive surface" as used herein refers without limitation to a surface of an electrode where an electrochemical reaction takes place. For example, at a predetermined potential, $H_2O_2$ reacts with the electroactive surface of a working electrode to produce two protons ($2H+$), two electrons ($2e^-$) and one molecule of oxygen ($O_2$), for which the electrons produce a detectable electronic current. The electroactive surface may include on at least a portion thereof, a chemically or covalently bonded adhesion promoting agent, such as aminoalkylsilane, and the like.

The term "subject" as used herein refers without limitation to mammals, particularly humans and domesticated animals.

The terms "interferants," "interferents" and "interfering species," as used herein refer without limitation to effects and/or species that otherwise interfere with a measurement of an analyte of interest in a sensor to produce a signal that does not accurately represent the analyte measurement. For example, in an electrochemical sensor, interfering species may be compounds with oxidation potentials that substantially overlap the oxidation potential of the analyte to be measured.

The phrase "enzyme layer" as used herein refers without limitation to a permeable or semi-permeable membrane comprising one or more domains that may be permeable to reactants and/or co-reactants employed in determining the analyte of interest. As an example, an enzyme layer comprises an immobilized glucose oxidase enzyme, which catalyzes an electrochemical reaction with glucose and oxygen to permit measurement of a concentration of glucose.

The term "membrane" as used herein refers to a semipermeable membrane that restricts or inhibits the flux of oxygen and other analytes through the semipermable membrane. Preferably, the membrane restricts or inhibits the flux of oxygen and other analytes from accessing the underlying enzyme layer. By way of example, for a glucose sensor, the membrane preferably renders oxygen in a non-rate-limiting excess. As a result, the upper limit of linearity of glucose measurement is extended to a much higher value than that which is achieved without the membrane.

The phrase "vinyl ester monomeric units" as used herein refers to compounds and compositions of matter which are formed from the polymerization of an unsaturated monomer having ester functionality. For example, polyethylene vinyl acetate polymer and copolymers thereof are compounds comprising vinyl ester monomeric units.

As used herein, the phrases "substantially absent" and "substantially free" mean at minimum, no amount of material will be deliberately added. Preferably, the amount of material present will be below detectable amounts or be present in trace amounts. More preferably, no amount of material will be present. For example, a sensor according to the present invention that is substantially absent a separate intervening hydrophilic layer between the electroactive surface and the interference layer will preferably be absent any intervening materials or layers between the electrode surface and the interference layer. Further, by way of example, an enzyme layer of the present invention that is "substantially free" of a cross-linking agent is either completely absent of cross-linking agent or its reaction products, or the enzyme layer comprises an amount of cross-linking agent resulting in insignificant cross-linking of the enzyme layer or of insufficient amounts of reaction products of the cross-linking agent with the enzyme or polymer.

Sensor System and Sensor Assembly

The aspects herein disclosed relate to the use of an analyte sensor system that measures a concentration of analyte of interest or a substance indicative of the concentration or presence of the analyte. The sensor system is a continuous device, and may be used, for example, as or part of a subcutaneous, transdermal (e.g., transcutaneous), or intravascular device. The analyte sensor may use an enzymatic, chemical, electrochemical, or combination of such methods for analyte-sensing. The output signal is typically a raw signal that is used to provide a useful value of the analyte of interest to a user, such as a patient or physician, who may be using the device. Accordingly, appropriate smoothing, calibration, and evaluation methods may be applied to the raw signal.

Generally, the sensor comprises at least a portion of an exposed electroactive surface of a working electrode surrounded by a plurality of layers. In one aspect, an interference layer is deposited over and in contact with at least a portion of the electroactive surface(s) of the sensor (working electrode(s) and optionally the reference electrode) to provide protection of the exposed electrode surface from the biological environment and/or limit or block interferents. An enzyme layer is deposited over and in contact with at least a portion of the interference layer. In one aspect, the interference layer and enzyme layer provides for rapid response and stabilization of the signal output of the sensor and/or eliminates the need to pre-treat the electroactive surface of the electrode with fugitive species, such as salts and electrolyte layers or domains, which simplifies manufacture and reduces lot-to-lot variability of the disclosed sensors. In another aspect, an interference layer, per se, is not used, and the enzyme layer covers at least a portion of the electroactive surfaces of the working electrode with optional additional layers covering at least a portion of the enzyme layer. In this aspect, a blank electrode may be used such that the signal produced from non-analyte interferents may be taken into account. The radiation stabilizing agent can be incorporated into any of the above layers.

One exemplary embodiment described in detail below utilizes a medical device, such as a catheter, with a glucose sensor assembly. In one aspect, a medical device with an analyte sensor assembly is provided for inserting the catheter into a subject's vascular system. The medical device with the analyte sensor assembly may include associated therewith an electronics unit associated with the sensor, and a receiver for receiving and/or processing sensor data. Although a few exemplary embodiments of continuous glucose sensors may be illustrated and described herein, it should be understood that the disclosed embodiments may be applicable to any device capable of substantially continual or substantially continuous measurement of a concentration of analyte of interest and for providing a rapid and accurate output signal that is representative of the concentration of that analyte.

Electrode and Electroactive Surface

The electrode and/or the electroactive surface of the sensor or sensor assembly disclosed herein comprises a conductive material, such as platinum, platinum-iridium, palladium, graphite, gold, carbon, conductive polymer, alloys, ink or the like. Although the electrodes can be formed by a variety of manufacturing techniques (bulk metal processing, deposition of metal onto a substrate, or the like), it may be advantageous to form the electrodes from screen printing techniques using conductive and/or catalyzed inks. The conductive inks may be catalyzed with noble metals such as platinum and/or palladium.

In one aspect, the electrodes and/or the electroactive surfaces of the sensor or sensor assembly are formed on a flexible substrate, such as a flex circuit. In one aspect, a flex circuit is part of the sensor and comprises a substrate, conductive traces, and electrodes. The traces and electrodes may be masked and imaged onto the substrate, for example, using screen printing or ink deposition techniques. The traces and the electrodes, and the electroactive surface of the electrodes may be comprised of a conductive material, such as platinum, platinum-iridium, palladium, graphite, gold, carbon, conductive polymer, alloys, ink or the like.

In one aspect, a counter electrode is provided to balance the current generated by the species being measured at the working electrode. In the case of a glucose oxidase based glucose sensor, the species being measured at the working electrode is $H_2O_2$. Glucose oxidase catalyzes the conversion of oxygen and glucose to hydrogen peroxide and gluconate according to the following reaction: Glucose+$O_2$→Gluconate+$H_2O_2$. Oxidation of $H_2O_2$ by the working electrode is balanced by reduction of any oxygen present, or other reducible species at the counter electrode. The $H_2O_2$ produced from the glucose oxidase reaction reacts at the surface of working electrode and produces two protons ($2H^+$), two electrons ($2e^-$), and one oxygen molecule ($O_2$).

In one aspect, additional electrodes may be included within the sensor or sensor assembly, for example, a three-electrode system (working, reference, and counter electrodes) and/or one or more additional working electrodes configured as a baseline subtracting electrode, or which is configured for measuring additional analytes. The two working electrodes may be positioned in close proximity to each other, and in close proximity to the reference electrode. For example, a multiple electrode system may be configured wherein a first working electrode is configured to measure a first signal comprising glucose and baseline and an additional working electrode substantially similar to the first working electrode without an enzyme disposed thereon is configured to measure a baseline signal consisting of baseline only. In this way, the baseline signal generated by the additional electrode may be subtracted from the signal of the first working electrode to produce a glucose-only signal substantially free of baseline fluctuations and/or electrochemically active interfering species.

In one aspect, the sensor comprises from 2 to 4 electrodes. The electrodes may include, for example, the counter electrode (CE), working electrode (WE1), reference electrode (RE) and optionally a second working electrode (WE2). In one aspect, the sensor will have at least a CE, RE and WE1. In one aspect, the addition of a WE2 is used, which may further improve the accuracy of the sensor measurement. In one aspect, the addition of a second counter electrode (CE2) may be used, which may further improve the accuracy of the sensor measurement.

The electroactive surface may be treated prior to application of any of the subsequent layers. Surface treatments may include for example, chemical, plasma or laser treatment of at least a portion of the electroactive surface. By way of example, the electrodes may be chemically or covalently contacted with one or more adhesion promoting agents. Adhesion promoting agents may include for example, aminoalkylalkoxysilanes, epoxyalkylalkoxysilanes and the like. For example, one or more of the electrodes may be chemically or covalently contacted with a solution containing 3-glycidoxypropyltrimethoxysilane.

In some alternative embodiments, the exposed surface area of the working (and/or other) electrode may be increased by altering the cross-section of the electrode itself. Increasing the surface area of the working electrode may be advantageous in providing an increased signal responsive to the analyte concentration, which in turn may be helpful in improving the signal-to-noise ratio, for example. The cross-section of the working electrode may be defined by any regular or irregular, circular or non-circular configuration.

Interference Layer

Interferants may be molecules or other species that may be reduced or oxidized at the electrochemically reactive surfaces of the sensor, either directly or via an electron transfer agent, to produce a false positive analyte signal (e.g., a non-analyte-related signal). This false positive signal generally causes the subject's analyte concentration to appear higher than the true analyte concentration. For example, in a hypoglycemic situation, where the subject has ingested an interferant (e.g., acetaminophen), the artificially high glucose signal may lead the subject or health care provider to believe that they are euglycemic or, in some cases, hyperglycemic. As a result, the subject or health care provider may make inappropriate or incorrect treatment decisions.

In one aspect, an interference layer is provided on the sensor or sensor assembly that substantially restricts or eliminates the passage of one or more interfering species. Interfering species for a glucose sensor include, for example, acetaminophen, ascorbic acid, bilirubin, cholesterol, creatinine, dopamine, ephedrine, ibuprofen, L-dopa, methyl dopa, salicylate, tetracycline, tolazamide, tolbutamide, triglycerides, urea and uric acid. The interference layer may be less permeable to one or more of the interfering species than to a target analyte species. The radiation stabilizing agent can be incorporated into any of the interference layers herein disclosed.

In an embodiment, the interference layer is formed from one or more cellulosic derivatives. In one aspect, mixed ester cellulosic derivatives may be used, for example, cellulose acetate butyrate, cellulose acetate phthalate, cellulose acetate propionate, cellulose acetate trimellitate, as well as their copolymers and terpolymers, with other cellulosic or non-cellulosic monomers, including cross-linked variations of the above. Other polymers, such as polymeric polysaccharides having similar properties to cellulosic derivatives, may be used as an interference material or in combination with the above cellulosic derivatives. Other esters of cellulose may be blended with the mixed ester cellulosic derivatives.

In one aspect, the interference layer is formed from cellulose acetate butyrate. Cellulose acetate butyrate is a cellulosic polymer having both acetyl and butyl groups, and hydroxyl groups. A cellulose acetate butyrate having about 35% or less acetyl groups, about 10% to about 25% butyryl groups, and hydroxyl groups making up the remainder may be used. A cellulose acetate butyrate having from about 25% to about 34% acetyl groups and from about 15 to about 20% butyryl groups may also be used, however, other amounts of acetyl and butyryl groups may be used. A preferred cellulose acetate butyrate contains from about 28% to about 30% acetyl groups and from about 16 to about 18% butyryl groups.

Cellulose acetate butyrate with a molecular weight of about 10,000 daltons to about 75,000 daltons is preferred, preferably from about 15,000, 20,000, or 25,000 daltons to about 50,000, 55,000, 60,000, 65,000, or 70,000 daltons, and more preferably about 65,000 daltons is employed. In certain embodiments, however, higher or lower molecular weights may be used or a blend of two or more cellulose acetate butyrates having different molecular weights may be used.

A plurality of layers of cellulose acetate butyrate may be combined to form the interference layer in some embodiments, for example, two or more layers may be employed. It may be desirable to employ a mixture of cellulose acetate butyrates with different molecular weights in a single solution, or to deposit multiple layers of cellulose acetate butyrate from different solutions comprising cellulose acetate butyrate of different molecular weights, different concentrations, and/or different chemistries (e.g., wt % functional groups). Additional substances in the casting solutions or dispersions may be used, e.g., casting aids, defoamers, surface tension modifiers, functionalizing agents, crosslinking agents, other polymeric substances, substances capable of modifying the hydrophilicity/hydrophobicity of the resulting layer, and the like.

The interference material may be sprayed, cast, coated, or dipped directly to the electroactive surface(s) of the sensor. The dispensing of the interference material may be performed using any known thin-film technique. Two, three or more layers of interference material may be formed by the sequential application and curing and/or drying of the casting solution.

The concentration of solids in the casting solution may be adjusted to deposit a sufficient amount of solids or film on the electrode in one layer (e.g., in one dip or spray) to form a layer sufficient to block an interferant with an oxidation or reduction potential otherwise overlapping that of a measured species (e.g., $H_2O_2$), measured by the sensor. For example, the casting solution's percentage of solids may be adjusted such that only a single layer is required to deposit a sufficient amount to form a functional interference layer that substantially prevents or reduces the equivalent glucose signal of the interferant measured by the sensor. A sufficient amount of interference material would be an amount that substantially prevents or reduces the equivalent glucose signal of the interferant of less than about 30, 20 or 10 mg/dl. By way of example, the interference layer is preferably configured to substantially block about 30 mg/dl of an equivalent glucose signal response that otherwise would be produced by acetaminophen by a sensor without an interference layer. Such equivalent glucose signal response produced by acetaminophen would include a therapeutic dose of acetaminophen. Any number of coatings or layers formed in any order may be suitable for forming the interference layer of the embodiments disclosed herein. The radiation stabilizing agent can be incorporated into any of the interference layers disclosed above.

In one aspect, the interference layer is deposited either directly onto the electroactive surfaces of the sensor or onto a material or layer in direct contact with the surface of the electrode. Preferably, the interference layer is deposited directly onto the electroactive surfaces of the sensor substantially without an intervening material or layer in direct contact with the surface of the electrode. It has been surprisingly found that configurations comprising the interference layer deposited directly onto the electroactive surface of the sensor substantially eliminates the need for an intervening layer between the electroactive surface and the interference layer while still providing a rapid and accurate signal representative of the analyte.

The interference layer may be applied to provide a thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 1, 1.5 or 2 microns to about 2.5 or 3 microns. Thicker membranes may also be desirable in certain embodiments, but thinner membranes may be generally preferred because they generally have a lower affect on the rate of diffusion of hydrogen peroxide from the enzyme membrane to the electrodes.

Enzyme Layer

The sensor or sensor assembly disclosed herein includes an enzyme layer. In one aspect, the enzyme layer is formed of a hydrophilic polymer-enzyme composition. For example, the enzyme layer comprises a hydrophilic polymer-enzyme composition deposited directly onto at least a portion of the electroactive surface.

In one aspect, the enzyme layer comprises an enzyme and a hydrophilic polymer selected from poly-N-vinylpyrrolidone (PVP), poly-N-vinyl-3-ethyl-2-pyrrolidone, poly-N-vinyl-4,5-dimethyl-2-pyrrolidone, polyacrylamide, poly-N,N-dimethylacrylamide, polyurethane, polyvinyl alcohol, polymers with pendent ionizable groups and copolymers thereof. Preferably, the enzyme layer comprises poly-N-vinylpyrrolidone. In other embodiments, the enzyme layer may comprise glucose oxidase, poly-N-vinylpyrrolidone and an amount of crosslinking agent sufficient to immobilize the enzyme.

The molecular weight of the hydrophilic polymer of the enzyme layer is such that fugitive species, including the radiation stabilizing agents, are prevented or substantially inhibited from leaving the sensor environment and more particularly, fugitive species are prevented or substantially inhibited from leaving the enzyme's environment when the sensor is initially deployed.

The hydrophilic polymer-enzyme composition of the enzyme layer can further include at least one protein and/or natural or synthetic material. For example, the hydrophilic polymer-enzyme composition of the enzyme layer may further include, for example, serum albumins, polyallylamines, polyamines and the like, as well as combination thereof.

The enzyme is preferably immobilized in the sensor. The enzyme can be encapsulated within the hydrophilic polymer and may be cross-linked or otherwise immobilized therein. Thus, the enzyme may be immobilized without cross-linking or producing cross-linking reaction products, as described below. The enzyme may be cross-linked or otherwise immobilized optionally together with at least one protein and/or natural or synthetic material. In one aspect, the hydrophilic polymer-enzyme composition comprises glucose oxidase, bovine serum albumin, and poly-N-vinylpyrrolidone. The composition may further include a cross-linking agent, for example, a dialdehyde such as glutaraldehdye, to cross-link or otherwise immobilize the components of the composition.

In one aspect, other proteins and/or natural or synthetic materials is substantially excluded from the hydrophilic polymer-enzyme composition of the enzyme layer. For example, the hydrophilic polymer-enzyme composition may be substantially free of bovine serum albumin Bovine albumin-free compositions may be desirable for meeting various governmental regulatory requirements. Thus, in one aspect, the enzyme layer comprises glucose oxidase and a sufficient amount of cross-linking agent, for example, a dialdehyde such as glutaraldehyde, to cross-link or otherwise immobilize the enzyme. In another aspect, the enzyme layer comprises glucose oxidase, poly-N-vinylpyrrolidone and a sufficient amount of cross-linking agent to cross-link or otherwise immobilize the enzyme.

In another aspect, the enzyme layer is substantially free of a cross-linking agent or the reaction products of a cross-linking agent and the hydrophilic polymer-enzyme composition. For example, the hydrophilic polymer-enzyme composition is substantially free of a dialdehyde cross-linking agent such as glutaraldehyde or contact therewith. Thus, in one aspect, the enzyme layer comprises glucose oxidase and a hydrophilic polymer, such as poly-N-vinylpyrrolidone, and is substantially free of a cross-linking agent or the reaction products of a cross-linking agent and the glucose oxidase or poly-N-vinylpyrrolidone. In another aspect, the enzyme layer comprises glucose oxidase, a hydrophilic polymer, such as poly-N-vinylpyrrolidone, and/or at least one protein and/or natural or synthetic material, such as bovine serum albumen, the enzyme layer being substantially free of a cross-linking agent or the reaction products of a cross-linking agent and the glucose oxidase, the poly-N-vinylpyrrolidone, or the at least one protein and/or natural or synthetic material.

The enzyme layer thickness may be from about 0.05 microns or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns. Preferably, the enzyme layer is deposited by spray or dip coating, however, other methods of forming the enzyme layer may be used. The enzyme layer may be formed by dip coating and/or spray coating one or more layers at a predetermined concentration of the coating solution, insertion rate, dwell time, withdrawal rate, and/or desired thickness. The radiation stabilizing agent can be incorporated into the enzyme layer, the hydrophilic polymer layer, or both the enzyme layer and hydrophilic polymer layer as disclosed above.

Flux Limiting Membrane

In one aspect, the sensor or sensor assembly further includes a membrane disposed over the subsequent layers described above, where the membrane alters or changes the rate of flux of one or more of the analytes of interest (e.g., "flux limiting membrane"). In aspects of the embodiments herein disclosed, the flux limiting membrane substantially prevents or eliminates components of the sensor membrane (e.g., enzymes, proteins, carriers, reaction products or low molecular weight membrane-related compounds) from that which it is disposed over from contacting the subject or the subject's immune system. Thus, the flux limiting membrane substantially "immobilizes" the materials and components of the membrane layers it is disposed over.

In some aspects, the flux limiting membrane can function as both an interferent layer and alter or change the rate of flux of one or more of the analytes of interest. For example, blends of siloxane polyurethanes (e.g., substantially hydrophobic siloxane polycarbonate polyurethanes) and hydrophilic polymers, (e.g., PVP) can be used as both the interference layer and flux limiting membrane. The radiation stabilizing agent can be incorporated into such blends.

Although the following description is directed to a membrane for a glucose sensor, the membrane may be modified for other analytes and co-reactants as well. In one aspect, the sensor or sensor assembly includes a membrane as herein disclosed. The radiation stabilizing agent can be incorporated into any of the flux limiting membranes herein disclosed.

In one aspect, the flux limiting membrane comprises a semi-permeable material that controls the flux of oxygen and glucose to the underlying enzyme layer, preferably providing oxygen in a non-rate-limiting excess. As a result, the upper limit of linearity of glucose measurement is extended to a much higher value than that which is achieved without the membrane. In one embodiment, the membrane exhibits an oxygen to glucose permeability ratio of from about 50:1 or less to about 400:1 or more, preferably about 200:1.

The material that comprises the membrane can be a vinyl polymer appropriate for use in sensor devices having sufficient permeability to allow relevant compounds to pass through it, for example, to allow an oxygen molecule to pass through in order to reach the active enzyme or electrochemical electrodes. Examples of materials which may be used to make the membrane include vinyl polymers having vinyl ester monomeric units. In a preferred embodiment, a flux limiting membrane comprises poly ethylene vinyl acetate (EVA polymer). In other aspects, the flux limiting membrane comprises poly(methylmethacrylate-co-butyl methacrylate) blended with the EVA polymer. The EVA polymer or its blends may be cross-linked, for example, with diglycidyl ether Films of EVA are very elastomeric, which may provide resiliency to the sensor for navigating a tortuous path, for example, into venous anatomy.

In one aspect of the invention, the flux limiting membrane substantially excludes condensation polymers such as silicone and urethane polymers and/or copolymers or blends thereof. Such excluded condensation polymers typically contain residual heavy metal catalytic material that may otherwise be toxic if leached and/or difficult to completely remove, thus rendering their use in such sensors undesirable for safety and/or cost.

The EVA polymer can be provided from a source having a composition anywhere from about 9 wt % vinyl acetate 12% vinyl acetate, 25% vinyl acetate, 33% vinyl acetate, up to about 40 wt % vinyl acetate. Other % amounts of vinyl acetate can be used. The EVA polymer is preferably dissolved in a solvent for dispensing on the sensor or sensor assembly. The solvent should be chosen for its ability to dissolve EVA polymer, to promote adhesion to the sensor substrate and enzyme electrode, and to form a solution that may be effectively applied (e.g. spray-coated or dip coated). Solvents such as cyclohexanone, paraxylene, and tetrahydrofuran may be suitable for this purpose. The solution may include about 0.5 wt % to about 6.0 wt % of the EVA polymer. In addition, the solvent should be sufficiently volatile to evaporate without undue agitation to prevent issues with the underlying enzyme, but not so volatile as to create problems with the spray process. In a preferred embodiment, the vinyl acetate component of the flux limiting membrane includes about 20% vinyl acetate. In preferred embodiments, the flux limiting membrane is deposited onto the enzyme layer to yield a layer thickness of from about 0.05 microns or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 5, 5.5 or 6 microns to about 6.5, 7, 7.5 or 8 microns. The flux limiting membrane may be deposited onto the enzyme layer by spray coating or dip coating. In one aspect, the flux limiting membrane is deposited on the enzyme layer by dip coating a solution of from about 1 wt. % to about 5 wt. % EVA polymer and from about 95 wt. % to about 99 wt. % solvent.

In one aspect of the invention, materials suitable for formation of a flux limiting membrane include polyvinylchloride, polystyrene, polyacrylate, polycarbonates, silicone rubber, polyesters, polyamides, vinylidene chloride, acrylonitrile, polyurethanes, polyvinylidene chloride, polyvinylidene chloride copolymerized with polyvinylchloride, polyvinyl butyryl, polyvinyl formal, polyvinyl acetate, polyvinyl alcohol, cellulose esters, and copolymers of the above materials, as well as glasses.

In some embodiments, plasticizers can be used in combination with the radiation stabilizer agents the preparation of any of the above membranes or layer, such as o-nitrophenyloctyl ether, dimethylphthalate, dioctylphenyl-phosphonate, dibutylphthalate, hexamethylphosphoramide, dibutyladipate, dioctylphthalate, diundecylphthalate, dioctyladipate, dioctyl sebacate, low and medium Mw mineral oils, and other conventional plasticizers. Such plasticizers can increase the mobility of the radiation stabilizing agents during their effective use.

Bioactive Agents

In some alternative embodiments, a bioactive agent may be optionally incorporated into the above described sensor system and in combination with the radiation stabilizing agent, such that the bioactive diffuses out into the biological environment adjacent to the sensor. Additionally or alternately, a bioactive agent may be administered locally at the exit-site or implantation-site. Additionally or alternately, a bioactive agent may be coated or otherwise contacted with one or more surfaces of the sensor. Suitable bioactive agents include those that modify the subject's tissue response to any of the sensor or components thereof. For example, bioactive agents can be selected from one or more of anti-inflammatory agents, anti-infective agents, antbiotics, anesthetics, inflammatory agents, growth factors, immunosuppressive agents, antiplatelet agents, anti-coagulants, anti-proliferates, ACE inhibitors, cytotoxic agents, anti-barrier cell compounds, vascularization-inducing compounds, and anti-sense molecules.

Radiation Stabilizing Agents

In one aspect of the invention, the sensor comprises one or more radiation stabilizing agents that contribute to radiation stability of the enzyme or one or more of the membrane layers of the sensor, and/or prevent or reduce high energy radiation related damage to the sensor, including but not limited to, the enzyme. In some embodiments of the invention, one or more of the electrode layer, the interference layer, the enzyme layer and/or the flux limiting membrane comprises one or more radiation stabilizing agents that contribute to radiation stability of the enzymes and bioactive agents of the sensor system.

Examples of radiation stabilizing agents include, for example, one or members from the hindered amines or hindered amine light stabilizers (HALS), hindered phenols, aromatic amines, sulfur containing compounds such as thioesters, and phosphorous containing compounds such as phosphate esters and phosphonites. Other suitable antioxidants include hydroxylamines and radical scavengers such as benzofuranone derivatives and acrylated bis-phenols. Other suitable radiation stabilizing compounds include ascorbic acid (Vitamin C), tocopherols (Vitamin E), UV absorbers, such as benzophenones, bezotriazoles, s-triazoles, and oxalanilides, and UV quenchers such as benzoate and substituted benzoates.

Suitable hindered phenols include, for example, 2,6-di-t-butyl-p-cresol; 4,4'-methylenebis(2,6-di-t-butylphenol); 4,4'-methylenebis(2,6-diisopropylphenol); 2,4,6-tri-t-butylphenol; 2,2'-thiobis-(4-methyl-6-t-butylphenol); 1,3,5-tris(4-t-butyl-3-hydroxy-2,6-dimethylbenzyl)-1,3,5-triazine-2,4,6-(1H,3H,5H)-trione; octadecyl 2(3',5'-di-t-butyl-4'hydroxyphenyl)propionate, tetrakis-(methylene-(3,5-di-(tert)-butyl-4-hydrocinnamate))methane (Irganox 1010), octadecyl 3,5-di-(tert)-butyl-4-hydroxycinnamate (Irganox 1076), etc; esters of thiodipropionic acid, such as dilauryl thiodipropionate and distearyl thiodipropionate, etc; hindered thiophenols such as 4,4'-thiobis(2-t-butyl-5-methylpheonol) (Lowinox TMB-6), 2,2'-thiobis(6-t-butyl-4-methylphenol) (Lowinox TBP-6), etc.; phosphites, such as triphenyl phosphite, trinonyl phosphite, diisodecyl pentaerythrityl diphosphite, diphenyldecyl phosphite, tris(2,4-di-t-buylphenyl)phosphite (Alkanox 240), and the like; and combinations thereof.

Suitable HALS include hindered piperidines, such as derivatives of 2,2,2,6-tetramethyl piperidine, for example, polymethylpropyl 3-oxy-[4(2,2,6,6 tetramethyl) piperidinyl] siloxane (Uvasil 299); poly[[.beta.-[1,1,3,3-tetramethyl butyl)amino]-s-triazine-2,4-diyl][[2,2,6,6-tetramethyl-4-piperidyl)imino]hexamethylene[(2,2,6,6,-tetramethyl-4-piperidyl)imino]] (Chimassorb 944); 1,3,5-triazine-2,4,6-triamine, N,N'''-[1,2-ethanediylbis[[[4.6-bis[butyl(1,2,2,6,6-pentamethyl-4-piperidinyl)amino]-1,3,5-triazine-2-yl] imino]-3,1 propanedyl]]-bis[N',N''-dibutyl-N',N''-bis(1,2,2,6,6-pentamethyl-4-piperidinyl)- (Chimassorb 119); alkyl substituted piperidinyl alkandioic acid esters such as bis(1,2,2,6,6-pentamethyl-4-piperidinyl)sebacate; bis-(1-octyloxy-2,2,6,6,tetramethyl-4-piperidinyl)sebacate (Tinuvin 123); bis (1,2,2,6,6-pentamethyl-4-piperidinyl)-[[3,5-bis(1,1-dimethylethyl)-4-hydroxyphenyl]methyl]butylmalonate (Tinuvin 144); 1,1'-(1,2-ethanediyl)bis(3,3,5,5-tetramethylpiperazinone); dimethyl succinate polymer with 4-hydroxy-2,2,6,6-tetramethyl-1-piperidineethanol (Tinuvin 622); poly((6-((1,1.3.3-tetramethylbutyl)amino)-s-triazine-2,4-diyl)(t-(2,2,6,6-tetramethyl-4-piperidyl)iminohexamethylene((2,2,6,6-tetramethyl-4-piperidyl)imino)) and dimethyl succinate polymer with 4-hydroxy 2,2,6,6-tetramethyl-1-piperidineethanol (Tinuvin 783); 1,3,5-Triazine-2,4,6-triamine, N2,N2'-1,2-ethanediylbis[N2-[3-[[4,6-bis[butyl(1,2,2,6,6-pentamethyl-4-piperidinyl)amino]-1,3,5-triazin-2-yl]amino]propyl]-N4,N6-dibutyl-N4,N6-bis(1,2,2,6,6-pentamethyl-4-piperidinyl) (Lowilite 19); polymer of dimethyl succinate and 4-hydroxy-2,2,6,6-tetramethyl-1-piperidine ethanol (Lowilite 62); bis(2,2,6,6-tetramethyl-4-piperidyl)sebacate (Lowilite 77); mixtures of bis(1,2,2,6,6-pentamethyl-4-piperidinyl)sebacate and methyl(1,2,2,6,6-pentamethyl-4-piperidinyl) sebacate (Lowilite 92); poly[[6-[(1,1,3,3-tetramethylbutyl)amino]-1,3,5-triazine-2,4-diyl]-[(2,2,6,6 tetramethyl-4-piperidyl)imino]hexamethylene[(2,2,6,6-tetramethyl-4-piperidyl)imino]] (Lowilite 94), and combinations or mixtures thereof.

In one aspect of the invention, the radiation stabilizing additive is physically or chemically incorporated into one or more membrane layers of the sensor assembly such as the interference layer, the enzyme layer, the flux limiting membrane, or the catheter. For example, the radiation stabilizing additive may be blended with the membrane layer and the additive-membrane blend may be sprayed, cast, coated, or dipped to the sensor assembly. The radiation stabilizing additive may also absorbed into the membrane, for example, by applying the additive to a surface of the membrane.

In some embodiments, the radiation stabilizing additive is further applied to the surface of the sensor, sensor housing, or any other surface of the sensor assembly which is exposed to radiation sterilization.

The loading of the radiation stabilizing agent can be determined based on the mode of sterilization, (e.g., the dose rate and exposure time), the location of the agent within the one or more membrane layers, the molecular weight of the agent, the diffusional properties of the agent in the one or more membrane layers, the synergistic effects of combination of agents and/or the membrane layer, and the cost of the agent. These parameters are readily determined by one of ordinary skill in the art. In one aspect, radiation stabilizing agents of molecular weight greater than about 1000 Daltons are preferred to minimize or reduce migration of the radiation stabilizing agent (e.g., "non-fugitive radiation stabilizing agents") through the membranes or layers of the sensors. Thus, polymeric radiation stabilizing agents, for example, polymeric HALS or polymers with multiple HALS or hindered phenolic appendages, are preferred.

Sensor Assembly Adapted for Intravenous Insertion

In one aspect, an electrochemical analyte sensor assembly may be configured for an intravenous insertion to a vascular system of a subject. In order to accommodate the sensor within the confined space of a device suitable for intravenous insertion, the sensor assembly may comprise a flexible substrate, such as a flex circuit. For example, the flexible substrate of the flex circuit may be configured as thin conductive electrodes coated on a non-conductive material such as a thermoplastic or thermoset. Conductive traces may be formed on the non-conductive material and electrically coupled to the thin conductive electrodes. The electrodes of the flex circuit may be as described above wherein the traces and contacts of flex circuit supports and electrically couples to the electrodes.

In other embodiments, the sensor assembly may comprise a plurality of wires. For example, the plurality of wires may be juxtaposed and coated or adhered together with an insulating material.

The sensor assembly may comprise at least one reference electrode and at least one working electrode, the at least one working electrode having an electroactive surface capable of providing a detectable electrical output upon interaction with an electrochemically detectable species. The sensor assembly may further comprise at least one counter electrode. In one aspect, the sensor assembly contains two or more working electrodes and two or more counter electrodes. In one aspect, the flex circuit contains two or more working electrodes, two or more blank electrodes and two or more counter electrodes.

Medical devices adaptable to the sensor assembly as described above include, but are not limited to a central venous catheter (CVC), a pulmonary artery catheter (PAC), a probe for insertion through a CVC or PAC or through a peripheral IV catheter, a peripherally inserted catheter (PICC), Swan-Ganz catheter, an introducer or an attachment to a Venous Arterial blood Management Protection (VAMP) system. Any size/type of Central Venous Catheter (CVC) or intravenous devices may be used or adapted for use with the sensor assembly.

For the foregoing discussion, the implementation of the sensor or sensor assembly is disclosed as being placed within a catheter; however, other devices as described above are envisaged and incorporated in aspects of the invention. The sensor assembly will preferably be applied to the catheter so as to be flush with the OD of the catheter tubing or the sensor may be recessed. This may be accomplished, for example, by thermally deforming or skiving the OD of the tubing to provide a recess for the sensor. The sensor assembly may be bonded in place, and sealed with an adhesive (e.g., urethane, 2-part epoxy, acrylic, etc.) that will resist bending/peeling, and adhere to the urethane CVC tubing, as well as the materials of the sensor. Small diameter electrical wires may be attached to the sensor assembly by soldering, resistance welding, or conductive epoxy. These wires may travel from the proximal end of the sensor, through one of the catheter lumens, and then to the proximal end of the catheter. At this point, the wires may be connected to an electrical connector, for example by solder or by ribbon cable with suitable connectors.

The sensor assembly as disclosed herein can be added to a catheter in a variety of ways. For example, an opening may be provided in the catheter body and a sensor or sensor assembly may be mounted inside the lumen at the opening so that the sensor would have direct blood contact. In one aspect, the sensor or sensor assembly may be positioned proximal to all the infusion ports of the catheter. In this configuration, the sensor would be prevented from or minimized in measuring otherwise detectable infusate concentration instead of the blood concentration of the analyte. Another aspect, an attachment method may be an indentation on the outside of the catheter body and to secure the sensor inside the indentation. This may have the added advantage of partially isolating the sensor from the temperature effects of any added infusate. Each end of the recess may have a skived opening to 1) secure the distal end of the sensor and 2) allow the lumen to carry the sensor wires to the connector at the proximal end of the catheter.

Preferably, the location of the sensor assembly in the catheter will be proximal (upstream) of any infusion ports to prevent or minimize IV solutions from affecting analyte measurements. In one aspect, the sensor assembly may be about 2.0 mm or more proximal to any of the infusion ports of the catheter.

In another aspect, the sensor assembly may be configured such that flushing of the catheter (e.g., saline solution) may be employed in order to allow the sensor assembly to be cleared of any material that may interfere with its function.

Sterilization of the Sensor or Sensor Assembly

Generally, the sensor or the sensor assembly as well as the device that the sensor is adapted to are sterilized before use, for example, in a subject. Sterilization may be achieved using radiation (e.g., electron beam or gamma radiation) or flash-UV sterilization, or other high energy radiation sterilization means known in the art.

Disposable portions, if any, of the sensor, sensor assembly or devices adapted to receive and contain the sensor preferably will be sterilized, for example using e-beam or gamma radiation or other know methods. The fully assembled device or any of the disposable components may be packaged inside a sealed non-breathable container or pouch.

Referring now to the Figures, FIG. 1A is an amperometric sensor 12. Sensor 12 is shown with working electrode 13 and at least one additional electrode, which can function as a blank electrode, a counter electrode and/or reference electrode, hereinafter referred to as the blank electrode 14. A membrane system is preferably deposited over the electrodes, such as described in more detail with reference to FIG. 1B, below.

In some embodiments, the sensor is formed from the working electrode 13 (e.g., a wire) and a blank electrode 14 positioned parallel to working electrode 13. The assembly of wires is optionally coated or adhered together with an insulating material 17, similar to that described below, so as to provide an insulating attachment. Certain portions of the electrodes are exposed to enable electrochemical reaction thereon, for example, a window can be formed in the insulator to expose a portion of the working electrode 13 for electrochemical reaction. In FIG. 1A, the electroactive portion of working electrode 13 is exposed at the end of the sensor 12.

The exposed electroactive portion of the working electrode 13 is configured to measure the concentration of an analyte. In an enzymatic electrochemical sensor for detecting glucose, for example, the working electrode measures the hydrogen peroxide produced by an enzyme catalyzed reaction of the analyte being detected and creates a measurable electronic current.

In some embodiments, each electrode is formed from a fine wire with a diameter D1 of from about 0.001 inches or less to about 0.010 inches or more, for example, and is formed from, e.g., a plated insulator, a plated wire, or bulk electrically conductive material.

In some embodiments, the working electrode comprises a wire formed from a conductive material, such as platinum, platinum-iridium, palladium, graphite, gold, carbon, conductive polymer, alloys, and the like. Although the electrodes can by formed by a variety of manufacturing techniques (bulk metal processing, deposition of metal onto a substrate, and the like), it can be advantageous to form the electrodes from plated wire (e.g., platinum on steel wire) or bulk metal (e.g., platinum wire). It is believed that electrodes formed from bulk metal wire provide superior performance (e.g., in contrast to deposited electrodes), including increased stability of assay, simplified manufacturability, resistance to contamination (e.g., which can be introduced in deposition processes), and improved surface reaction (e.g., due to purity of material) without peeling or delamination.

In some embodiments, the working electrode 13 is covered with an insulating material, for example, a non-conductive polymer. Dip-coating, spray-coating, vapor-deposition, or other coating or deposition techniques can be used to deposit the insulating material on the working electrode. In one embodiment, the insulating material comprises parylene, which can be an advantageous polymer coating for its strength, lubricity, and electrical insulation properties. Generally, parylene is produced by vapor deposition and polymerization of para-xylylene (or its substituted derivatives). While not wishing to be bound by theory, it is believed that the lubricious (e.g., smooth) coating (e.g., parylene) on the sensors of some embodiments contributes to minimal trauma and extended sensor life. While parylene coatings are generally preferred in some embodiments, any suitable insulating material can be used, for example, fluorinated polymers, polyethyleneterephthalate (PET), polyurethane, polyimide, other nonconducting polymers, and the like. Glass or ceramic materials can also be employed. Other materials suitable for use include surface energy modified coating systems such as are marketed under the trade names AMC18, AMC148, AMC141, and AMC321 by Advanced Materials Components Express of Bellafonte, Pa. In some alternative embodiments, however, the working electrode may not require a coating of insulator.

The blank electrode 14 is formed from the same electrode materials as the working electrode 13 and has the same membrane system, as described with regard to FIG. 1B below, but does not contain the enzyme of the working electrode 13. The blank electrode 14 is used as a reference to eliminate any background noise (e.g., a component of a analyte sensor signal that is not related to the analyte concentration). In addition, a reference electrode (not pictured) may be used. The reference electrode, which can function as a reference electrode alone, or as a dual reference and counter electrode, is formed from silver, silver/silver chloride, and the like. In some embodiments, the reference electrode is juxtapositioned; however other configurations are also possible (e.g., coiled within the fluid connector, or an intradermal or on-skin reference electrode or twisted with or around the working electrode). In the illustrated embodiments, the blank electrode 14 is positioned parallel to the working electrode 13.

In some embodiments, a silver wire is formed onto the sensor as described above, and subsequently chloridized to form silver/silver chloride reference electrode. Advantageously, chloridizing the silver wire as described herein enables the manufacture of a reference electrode with optimal in vivo performance. Namely, by controlling the quantity and amount of chloridization of the silver to form silver/silver chloride, improved break-in time, stability of the reference electrode, and extended life has been shown with some embodiments. Additionally, use of silver chloride as described above allows for relatively inexpensive and simple manufacture of the reference electrode.

In embodiments wherein an outer insulator is disposed, a portion of the coated assembly structure can be stripped or otherwise removed, for example, by hand, excimer lasing, chemical etching, laser ablation, grit-blasting (e.g., with sodium bicarbonate or other suitable grit), and the like, to expose the electroactive surfaces. Alternatively, a portion of the electrode can be masked prior to depositing the insulator in order to maintain an exposed electroactive surface area. In one exemplary embodiment, grit blasting is implemented to expose the electroactive surfaces, preferably utilizing a grit material that is sufficiently hard to ablate the polymer material, while being sufficiently soft so as to minimize or avoid damage to the underlying metal electrode (e.g., a platinum electrode). Although a variety of "grit" materials can be used (e.g., sand, talc, walnut shell, ground plastic, sea salt, and the like), in some preferred embodiments, sodium bicarbonate is an advantageous grit-material because it is sufficiently hard to ablate, e.g., a parylene coating, without damaging, e.g., an underlying platinum conductor. One additional advantage of sodium bicarbonate blasting includes its polishing action on the metal as it strips the polymer layer, thereby eliminating a cleaning step that might otherwise be necessary.

Figure 1B:
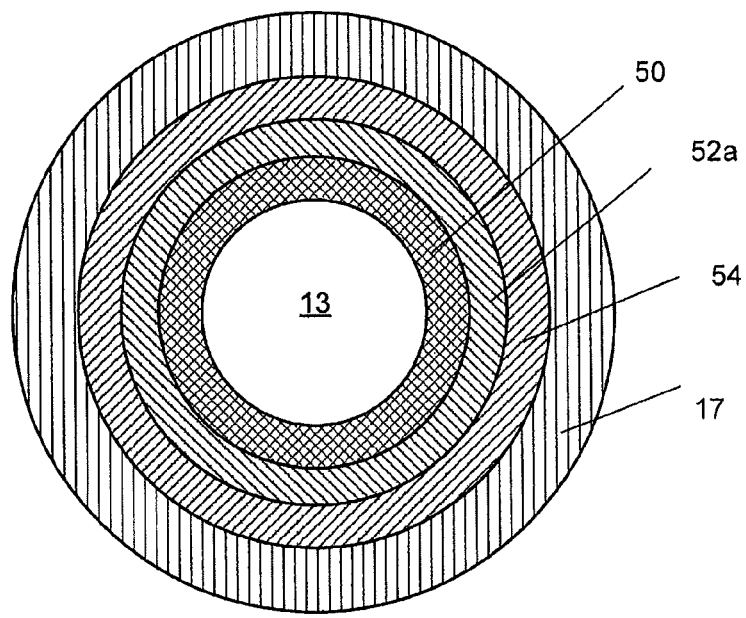
FIG. 1B is a side cross-sectional view of a working electrode portion of the sensor of FIG. 1A.

FIG. 1B depicts a cross-sectional view of sensor 12 shown in FIG. 1A in the vicinity of the working electrode 13 of an embodiment disclosed herein. The working electrode 13 may be at least partially coated with an interference layer 50. Interference layer 50 may be at least partially coated with an enzyme layer 52a that is selected to chemically react when the sensor is exposed to certain reactants, for example, found in the bloodstream. For example, in an embodiment for a glucose sensor, enzyme layer 52a may contain glucose oxidase, such as may be derived from *Aspergillus niger* (EC 1.1.3.4), for example, type II, type VII, or type X. Layer 52b of the blank electrode 14 does not contain enzymes.

Flux limiting membrane 54 covers enzyme layer 52a and interference layer 50 and at least a portion of working electrode 13. Flux limiting membrane 54 may selectively allow diffusion, from blood to the enzyme layer 52a, a blood component that reacts with the enzyme. In a glucose sensor embodiment, the flux limiting membrane 54 passes an abundance of oxygen, and selectively limits glucose, to the enzyme layer 52a. In addition, a flux limiting membrane 54 that has adhesive properties may mechanically seal the enzyme layer 52a to the sub-layers and/or working electrode 13, and may also seal the working electrode 13 to the sensor substrate 13. It is herein disclosed that a flux limiting membrane formed from an EVA polymer may serve as a flux limiter at the top of the electrode, but also serve as a sealant or encapsulant at the enzyme/electrode boundary and at the electrode/substrate boundary. An additional biocompatible layer (not shown), including a biocompatible anti-thrombotic substance such as heparin, may be added onto the flux limiting membrane 54.

Figure 1C:
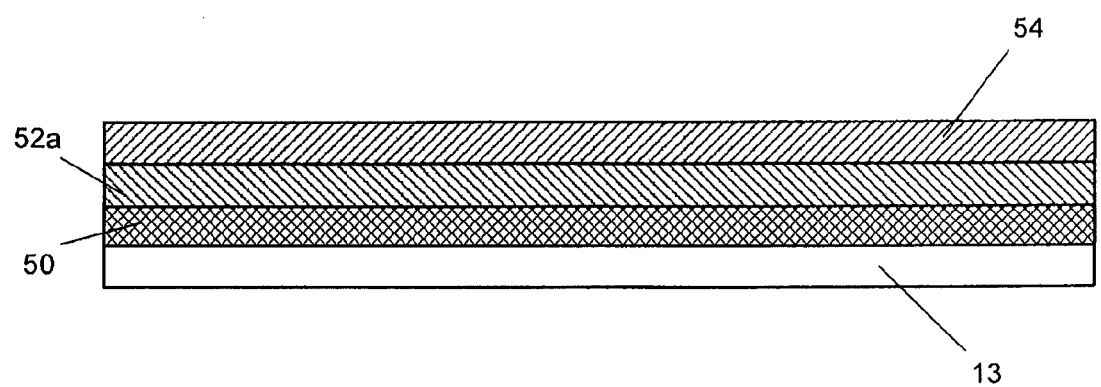
FIG. 1C is a side view of a working electrode portion of a planar sensor according to an aspect disclosed and described.

FIG. 1C depicts a cross sectional view of a portion of a working electrode in an embodiment disclosed herein. In the exemplary embodiment, a window is formed through the insulating material 17 to expose an electroactive surface of the working electrode. The window may be a radial window to expose the circumferential electroactive surface of the electrode or the window may be any other shaped window formed through the insulating material 17, such as a rectangular cut out. In the illustrated cross sectional embodiment, flux limiting membrane 54, beneath which are positioned enzyme layer 52a, interference layer 50, and working electrode 13. Additionally, sections of electroactive surface of a reference electrode or blank electrode 14 are exposed. For example, the sections of electroactive surface can be masked during deposition of an outer insulating layer or etched after deposition of an outer insulating layer.

Referring now to FIGS. 2-3, aspects of the sensor adapted to a central line catheter with a sensor or sensor assembly are discussed as exemplary embodiments, without limitation to any particular intravenous device. FIG. 2 shows a sensor assembly within a multi-lumen catheter. The catheter assembly 10 may include multiple infusion ports 11a, 11b, 11c, 11d and one or more electrical connectors 130 at its most proximal end. A lumen 15a, 15b, 15c, or 15d may connect each infusion port 11a, 11b, 11c, or 11d, respectively, to a junction 190. Similarly, the conduit 170 may connect an electrical connector 130 to the junction 190, and may terminate at junction 190, or at one of the lumens 15a-15d (as shown). Although the particular embodiment shown in FIG. 2 is a multi-lumen catheter having four lumens and one electrical connector, other embodiments having other combinations of lumens and connectors are possible, including a single lumen catheter, a catheter having multiple electrical connectors, etc. In another embodiment, one of the lumens and the electrical connector may be reserved for a probe or other sensor mounting device, or one of the lumens may be open at its proximal end and designated for insertion of the probe or sensor mounting device.

The distal end of the catheter assembly 10 is shown in greater detail in FIG. 3. At one or more intermediate locations along the distal end, the tube 21 may define one or more ports formed through its outer wall 23. These may include the intermediate ports 25*a*, 25*b*, and 25*c*, and an end port 25*d* that may be formed at the distal tip of tube 21. Each port 25*a*-25*d* may correspond respectively to one of the lumens 15*a*-15*d*. That is, each lumen may define an independent channel extending from one of the infusion ports 11*a*-11*d* to one of the tube ports 25*a*-25*d*. The sensor assembly may be presented to the sensing environment via positioning at one or more of the ports to provide contact with the medium to be analyzed.

Central line catheters may be known in the art and typically used in the Intensive Care Unit (ICU)/Emergency Room of a hospital to deliver medications through one or more lumens of the catheter to the patient (different lumens for different medications). A central line catheter is typically connected to an infusion device (e.g. infusion pump, IV drip, or syringe port) on one end and the other end inserted in one of the main arteries or veins near the patient's heart to deliver the medications. The infusion device delivers medications, such as, but not limited to, saline, drugs, vitamins, medication, proteins, peptides, insulin, neural transmitters, or the like, as needed to the patient. In alternative embodiments, the central line catheter may be used in any body space or vessel such as intraperitoneal areas, lymph glands, the subcutaneous, the lungs, the digestive tract, or the like and may determine the analyte or therapy in body fluids other than blood. The central line catheter may be a double lumen catheter. In one aspect, an analyte sensor is built into one lumen of a central line catheter and is used for determining characteristic levels in the blood and/or bodily fluids of the user. However, it will be recognized that further embodiments may be used to determine the levels of other agents, characteristics or compositions, such as hormones, cholesterol, medications, concentrations, viral loads (e.g., HIV), or the like. Therefore, although aspects disclosed herein may be primarily described in the context of glucose sensors used in the treatment of diabetes/diabetic symptoms, the aspects disclosed may be applicable to a wide variety of patient treatment programs where a physiological characteristic is monitored in an ICU, including but not limited to blood gases, pH, temperature and other analytes of interest in the vascular system.

In another aspect, a method of intravenously measuring an analyte in a subject is provided. The method comprises providing a catheter comprising the sensor assembly comprising the radiation stabilizing agent as described herein and introducing the catheter into the vascular system of a subject. The method further comprises measuring an analyte.

In another aspect, a method of stabilizing an enzyme based analyte sensor from high energy radiation is provided. The method comprises providing an enzyme-based analyte sensor, the sensor comprising at least one enzyme, and at least one radiation stabilizing agent in an amount sufficient to stabilize the enzyme to an amount of high energy radiation sufficient to sterilize the enzyme-based analyte sensor. In one aspect, an intravenous analyte sensor, for example, an intravenous blood glucose sensor (IVBG) suitable for surgical and/or ICU deployment in a subject is provided. The method further comprises introducing the catheter into the vascular system of a subject. The method further comprises measuring an analyte of interest and optionally displaying the measurement to the user.

Accordingly, sensors and methods have been provided for measuring an analyte in a subject, including a sensor assembly configured for adaption to a continuous glucose monitoring device or a catheter for insertion into a subject's vascular system having electronics unit electrically configurable to the sensor assembly.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The above description discloses several methods and materials. These descriptions are susceptible to modifications in the methods and materials, as well as alterations in the fabrication methods and equipment. Such modifications will become apparent to those skilled in the art from a consideration of this disclosure or practice of the disclosure. Consequently, it is not intended that this disclosure be limited to the specific embodiments disclosed herein, but that it cover all modifications and alternatives coming within the true scope and spirit of the claims.

What is claimed is:

1. An enzyme-based analyte sensor comprising at least one enzyme and at least one non-fugitive radiation stabilizing agent
   wherein the radiation stabilizing agent comprises at least one of a hindered amine light stabilizer, a polymeric hindered phenol, a polymeric aromatic amine, a polymer with thioester or phosphorous containing appendages, a polymeric hydroxyl amine, a polymeric benzofuranone derivative, and polymeric acrylated bis-phenol,
   wherein the molecular weight of the radiation stabilizing agent is greater than about 1000 Daltons and the radiation stabilizing agent is present in an amount sufficient to stabilize the activity of the at least one enzyme when the sensor is subjected to high energy radiation.

2. The enzyme-based analyte sensor of claim 1, wherein the hindered amine light stabilizer comprises one or more of polymethylpropyl 3-oxy-[4(2,2,6,6 tetramethyl) piperidinyl] siloxane (Uvasil 299); poly[[.beta.-[1,1,3,3-tetramethyl butyl)amino]-s-triazine-2,4-diyl][[2,2,6,6-tetramethyl-4-piperidyl)imino]-hexamethylene[(2,2,6,6,-tetramethyl-4-piperidyl)imino]] (Chimassorb 944); dimethyl succinate polymer with 4-hydroxy-2,2,6,6-tetramethyl-1-piperidineethanol (Tinuvin 622); poly((6-((1,1.3.3-tetramethylbutyl)amino)-s-triazine-2,4-diyl)(t-(2,2,6,6-tetramethyl-4-piperidyl)imino-hexa-methylene((2,2,6,6-tetramethyl-4-piperidyl)imino)) and dimethyl succinate polymer with 4-hydroxy 2,2,6,6-tetramethyl-1-piperidineethanol (Tinuvin 783); polymer of dimethyl succinate and 4-hydroxy-2,2,6,6-tetramethyl-1-piperidine ethanol (Lowilite 62).

3. The enzyme-based analyte sensor of claim 1 or 2, further comprising an interference layer.

4. The enzyme-based analyte sensor of claim 3, wherein the interference layer comprises the at least one radiation stabilizing agent.

5. The enzyme-based analyte sensor of claim 1 or 2 comprising a flux limiting membrane.

6. The enzyme-based analyte sensor of claim 5, wherein the flux limiting membrane comprises the at least one radiation stabilizing agent.

7. The enzyme-based analyte sensor of claim 1, wherein the enzyme based analyte sensor is configured for a catheter.

8. The enzyme-based analyte sensor of claim 1, wherein the enzyme is presented in an enzyme layer, the enzyme layer comprising a hydrophilic polymer.

9. The enzyme-based analyte sensor of claim 8, wherein the hydrophilic polymer comprises at least one of a poly-N-vinylpyrrolidone, a poly-N-vinyl-3-ethyl-2-pyrrolidone, a poly-N-vinyl-4,5-dimethyl-2-pyrrolidone, a polyvinylimidazole, a poly-N—N-dimethylacrylamide, a polyacrylamide, and copolymers thereof.

10. The enzyme-based analyte sensor of claim 8, wherein the hydrophilic polymer is poly-N-vinylpyrrolidone.

11. The enzyme-based analyte sensor of claim 8, wherein the enzyme is glucose oxidase, the hydrophilic polymer is poly-N-vinylpyrrolidone, and the enzyme layer comprises the at least one radiation stabilizing agent.

12. The enzyme-based analyte sensor of claim 1 or 2 comprising a flux limiting membrane and an interference layer.

13. The enzyme-based analyte sensor of claim 12 wherein the flux limiting membrane, interference layer or both comprise the at least one radiation stabilizing agent.

* * * * *